United States Patent [19]

Suzuki

[11] 4,161,612
[45] Jul. 17, 1979

[54] PROCESS FOR PREPARING THIODIGLYCOLIC ACID

[75] Inventor: Shigeto Suzuki, San Francisco, Calif.

[73] Assignee: Chevron Research Company, San Francisco, Calif.

[21] Appl. No.: 892,246

[22] Filed: Mar. 31, 1978

[51] Int. Cl.$^2$ ............................................. C07C 149/20
[52] U.S. Cl. ...................................... 562/594; 562/603
[58] Field of Search ...................... 260/537 S; 562/594

[56] References Cited

U.S. PATENT DOCUMENTS

| | | | |
|---|---|---|---|
| 2,425,226 | 8/1947 | Bearse | 260/537 S |
| 3,665,035 | 5/1972 | Rice et al. | 260/537 S |
| 3,753,913 | 8/1973 | Jarwenko | 260/537 S |

Primary Examiner—Vivian Garner
Attorney, Agent, or Firm—D. A. Newell; John Stoner, Jr.; A. T. Bertolli

[57] ABSTRACT

A process for preparing thiodiglycolic acid comprises contacting bromoacetic acid, diglycolic acid or glycolic acid and hydrogen sulfide in the presence of aqueous hydrogen bromide.

9 Claims, No Drawings

PROCESS FOR PREPARING THIODIGLYCOLIC ACID

BACKGROUND OF THE INVENTION

The invention concerns a process for preparing thiodiglycolic acid directly from bromoacetic acid, diglycolic acid or glycolic acid by contacting one of these acids or a mixture of these acids and hydrogen sulfide in the presence of aqueous hydrogen bromide.

Thiodiglycolic acid (thiodiacetic acid or thioethanoic acid) has the proposed molecular structure $$HOOCCH_2-S-CH_2COOH$$

is a white solid and melts at about 130° C. The currently accepted process for preparing thiodiglycolic acid calls for reacting sodium sulfide and sodium chloroacetate followed by acidification. Thiodiglycolic acid can also be prepared together with thioglycolic acid by the reaction of glycolic acid with hydrogen sulfide in the presence of silver oxide. These and other processes in which thiodiglycolic acid is a by-product are discussed in Kirk Othmer, *Encyclopedia of Chemical Technology*, Vol. 20, pages 198 et seq. (1967) 2nd Edition.

Thiodiglycolic acid salts can be used in hair-waving preparations, particularly the ammonium salt. The calcium salt can be used in depilatory compositions. The color reaction of thioglycolates and diglycolates with iron salts is the basis for qualitative tests for iron.

SUMMARY OF THE INVENTION

It has now been found that thiodiglycolic acid can be prepared by the aqueous hydrogen bromide catalyzed reaction of bromoacetic acid, diglycolic acid, glycolic acid, or mixtures thereof and hydrogen sulfide at a temperature of from about 90° C. to about 220° C. and a pressure of from about 0.1 atmosphere to about 100 atmospheres.

DETAILED DESCRIPTION OF THE INVENTION

Among other factors, the process of this invention is based upon the discovery that aqueous hydrogen bromide will catalyze the reaction of bromoacetic acid, diglycolic acid or glycolic acid and hydrogen sulfide to produce good yields of thiodiglycolic acid. The discovery is particularly surprising in view of the fact that hydrogen chloride and hydrogen iodide give only insignificant amounts of thioglycolic acid.

Glycolic, bromoacetic or diglycolic acid and hydrogen sulfide, the essential materials of the process of this invention, are readily available commodity chemicals. Glycolic and diglycolic acids can be prepared by the acid catalyzed reaction of aqueous formaldehyde and a synthesis gas comprising carbon monoxide and hydrogen. U.S. Pat. No. 3,911,003, granted Oct. 7, 1975 to S. Suzuki, describes this process using hygrogen fluoride as the acid catalyst. Bromoacetic acid can be prepared by the reaction of glycolic acid and hydrogen bromide. Hydrogen sulfide is currently available as a by-product of petroleum refining, or by the direct reaction of hydrogen and sulfur.

The process of this invention must be carried out using an aqueous hydrogen bromide catalyst. Hydrogen bromide gas is soluble in water, as is hydrogen sulfide. Hydrobromic acid is commercially available as a 48% solution of hydrogen bromide in water. Accordingly, the process can be carried out by contacting glycolic acid and hydrogen sulfide in aqueous hydrobromic acid. The stoichiometric requirements of the reaction are satisfied by contacting two moles of glycolic acid with one mole of hydrogen sulfide. However, in practice it is preferable to use an excess of hydrogen sulfide. Accordingly, the mole ratio of hydrogen sulfide to glycolic acid preferably ranges from about 0.4 to about 20, most preferably from about 0.5 to about 10.

A catalytic amount of hydrogen bromide is required. Catalytic amounts range from about 5 mol percent to about 400 mol percent on gylcolic acid values employed. In practice, it is preferable to carry out the process using an aqueous solution of hydrogen bromide as the reaction medium. Thus, the concentration of hydrogen bromide preferably varies from about 5 percent by weight to about 50 percent by weight, and the concentration of water ranges from about 1 percent by weight to about 50 percent by weight.

The process is carried out at a temperature from about 90° C. to about 220° C., preferably from about 100° C. to about 180° C., or about 120° C. to about 160° C.; and a pressure from about 0.1 atmosphere to about 100 atmospheres, preferably from about 10 atmospheres to about 50 atmospheres or about 10 atmospheres to about 40 atmospheres. While the process can be carried out in batch fashion, continuous processing is preferable. The reaction product may contain some bromoacetic acid, which, if continuous processing is used, can be recycled to the reaction zone providing essentially quantitative yields. However, complete conversion of the glycolic acid to product is preferred. Thus, in a preferred embodiment, glycolic acid and hydrogen sulfide are contacted in aqueous hydrogen bromide using conventional acid-resistant equipment maintained at a temperature of about 150° C. and a pressure of about 30 atmospheres, the mole ratio of hydrogen sulfide to glycolic acid being about 3 and the concentration of hydrogen bromide being 20% by weight of the total reaction mixture. The product stream, after $H_2S$ venting, contains water, HBr and thiodiglycolic acid and is refined in conventional manner first by distillation to remove aqueous HBr, followed by crystallization.

EXAMPLES

The following examples further illustrate the process of this invention and suggest alternative embodiments. The examples should not be interpreted as limiting the scope of the invention.

EXAMPLE 1

A 300-ml capacity, stainless steel reactor with a glass liner was charged with 0.1 mol of glycolic acid, 10 ml of 48% aqueous HBr (containing 0.09 mol of HBr and 0.4 mol of $H_2O$), and 0.38 mol of $H_2S$. The reactor was sealed and heated at 145°–148° C. for 2 hours while the reaction mixture was magnetically stirred. The maximum pressure reached was 400 psig. The reactor was cooled, vented, and most aqueous HBr was stripped off from the reaction mixture to obtain 8.9 grams of crude thiodiglycolic acid (pale yellow solid) which was methylated in refluxing methanol with a catalytic amount of sulfuric acid followed by analyses by gas chromatogram (5% FFAP column) which showed over 99% conversion of the glycolic acid to thioglycolic acid in at least 95% selectivity.

The above procedure was repeated using 0.1 mol of glycolic acid, 0.36 mol of hydrogen bromide, 1.7 mol of water, and 0.28 mol of hydrogen sulfide at a temperature of 120° C. and a maximum pressure of 280 psig. 63% of the glycolic acid was converted to thioglycolic acid in 16% yield, and to bromoacetic acid in 81% yield. This procedure was repeated using 0.24 mol of hydrogen sulfide at 150° C. and a maximum pressure of 360 psig. 99% of the glycolic acid was converted to thiodiglycolic acid in over 95% yield.

EXAMPLE 2

The same reactor used in Example 1 was charged with 0.1 mol of bromoacetic acid, 40 ml of 48% aqueous HBr (containing 0.36 mol of HBr and 2.7 mols of $H_2O$), and 0.32 mol of $H_2S$, and the mixture was reacted at 110°–120° C. for 3 hours. The product was worked up and analyzed as before to show 86% conversion of bromoacetic acid with 93% selectivity to thiodiglycolic acid.

EXAMPLE 3

The same reactor used in Example 1 was charged with 0.1 mol of glycolic acid, 3 ml of 48% aqueous HBr (containing 0.0267 mol of HBr and 0.13 mol of $H_2O$), and 0.36 mol of $H_2S$, and the mixture was reacted at 150° C. for 2 hours. The product mixture was worked up and analyzed as before to show 75% conversion of glycolic acid to thiodiglycolic acid with 95% selectivity.

EXAMPLE 4

The same reactor used in Example 1 was charged with 0.1 mol of diglycolic acid, 21 ml of 48% aqueous HBr (containing 0.187 mol of HBr and 0.091 mol of $H_2O$), and 0.40 mol of $H_2S$, and the mixture was reacted at 150° C. for 2 hours. The product was worked up and analyzed as before to show 99% conversion of diglycolic acid to thiodiglycolic acid with about 60% selectivity.

COMPARATIVE EXAMPLE

The same reactor used in Example 1 was charged with 0.1 mol of glycolic acid, 20 grams of 50% aqueous HI (containing 0.08 mol of HI and 0.56 mol of $H_2O$), and 0.32 mol of $H_2S$, and the mixture was heated at 150° C. for 4 hours. The product was worked up and analyzed as before to show complete conversion of glycolic acid but with no formation of thiodiglycolic acid or iodoacetic acid.

COMPARATIVE EXAMPLE 2

The same reactor used in Example 1 was charged with 0.1 mol of glycolic acid, 10 grams of 37% aqueous HCl (containing 0.10 mol of HCl and 0.36 mol of $H_2O$), and 0.35 mol of $H_2S$, and the mixture was reacted at 150° C. for 4 hours. The product was worked up and analyzed as before to show less than 1% conversion of glycolic acid to thiodiglycolic acid.

What is claimed is:

1. A process for preparing thiodiglycolic acid which comprises contacting glycolic acid, diglycolic acid or bromoacetic acid and hydrogen sulfide in the presence of aqueous hydrogen bromide at a temperature of from about 90° C. to about 220° C. and a pressure of from about 0.1 atmosphere to about 100 atmospheres.

2. A process according to claim 1 wherein the mole ratio of hydrogen sulfide to acid is from about 0.4 to about 20, and the concentration of hydrogen bromide is from about 5 to about 50 percent by weight of total reaction mixture.

3. A process according to claim 2 wherein the mole ratio of hydrogen sulfide to acid is from about 0.5 to about 10, and the concentration of hydrogen bromide is from about 5 to about 50 percent by weight of total reaction mixture.

4. A process according to claim 1 wherein the temperature is from about 100° C. to about 180° C. and the pressure is from about 10 atmospheres to about 50 atmospheres.

5. A process for preparing thiodiglycolic acid which comprises contacting glycolic acid and hydrogen sulfide in the presence of aqueous hydrogen bromide at a temperature of from about 100° C. to about 180° C. and a pressure of from about 10 atmospheres to about 50 atmospheres; separating a thiodiglycolic acid product fraction and a bromoacetic acid product fraction; and recycling the bromoacetic acid fraction to the reaction zone.

6. A process according to claim 5 wherein the temperature is from about 120° C. to about 160° C. and the pressure is from about 10 atmospheres to about 40 atmospheres.

7. A process according to claim 5 wherein the mole ratio of hydrogen sulfide to glycolic acid is from about 0.4 to about 20, and the concentration of hydrogen bromide is from about 5 percent by weight to about 50 percent by weight of total reaction mixture.

8. A process according to claim 5 wherein the mole ratio of hydrogen sulfide to glycolic acid is from about 0.5 to about 10, and the concentration of hydrogen bromide is from about 5 percent by weight to about 50 percent by weight of total reaction mixture.

9. A process according to claim 5 wherein the temperature is about 150° C., the pressure is about 30 atmospheres, the mole ratio of hydrogen sulfide to glycolic acid is about 3, and the concentration of hydrogen bromide is 20 percent by weight of total reaction mixture.

* * * * *